US 8,454,563 B2

(12) United States Patent
Insignares et al.

(10) Patent No.: US 8,454,563 B2
(45) Date of Patent: Jun. 4, 2013

(54) TROCAR AND CANNULA ASSEMBLY HAVING IMPROVED CONICAL VALVE, AND METHODS RELATED THERETO

(76) Inventors: Rogelio A. Insignares, Winter Park, FL (US); Kenneth M. Roger, Casselberry, FL (US); Gary Wayne Haberland, Winter Park, FL (US); Roland Strelitzki, Altamonte Springs, FL (US)

( * ) Notice: Subject to any disclaimer, the term of this patent is extended or adjusted under 35 U.S.C. 154(b) by 226 days.

(21) Appl. No.: 12/901,393

(22) Filed: Oct. 8, 2010

(65) Prior Publication Data
US 2011/0087170 A1    Apr. 14, 2011

Related U.S. Application Data

(60) Provisional application No. 61/250,194, filed on Oct. 9, 2009.

(51) Int. Cl.
*A61B 17/34* (2006.01)
(52) U.S. Cl.
USPC ............................. 604/167.03; 604/6.1
(58) Field of Classification Search
USPC ............... 604/6.1, 34, 99.04, 167.03, 236, 604/288.03, 323, 335; 623/1.24
See application file for complete search history.

(56) References Cited

U.S. PATENT DOCUMENTS

| | | |
|---|---|---|
| 3,939,835 A | 2/1976 | Bridgman |
| 4,056,116 A | 11/1977 | Carter et al. |
| 4,486,024 A | 12/1984 | Cooper |
| 4,493,319 A | 1/1985 | Pol et al. |
| 4,723,550 A | 2/1988 | Bales et al. |
| 4,842,591 A | 6/1989 | Luther |
| 4,943,280 A | 7/1990 | Lander |
| 4,960,412 A | 10/1990 | Fink |
| 5,104,383 A | 4/1992 | Shichman |
| 5,125,553 A | 6/1992 | Oddsen et al. |
| 5,127,909 A | 7/1992 | Shichman |
| 5,141,498 A | 8/1992 | Christian |
| 5,150,702 A | 9/1992 | Miyanaga et al. |
| 5,167,636 A | 12/1992 | Clement |
| 5,194,383 A | 3/1993 | Tsai et al. |
| 5,197,955 A | 3/1993 | Stephens et al. |
| 5,209,737 A | 5/1993 | Ritchart et al. |
| 5,217,468 A | 6/1993 | Clement |
| 5,220,928 A | 6/1993 | Oddsen et al. |
| 5,226,891 A | 7/1993 | Bushatz et al. |
| 5,250,065 A | 10/1993 | Clement et al. |
| 5,251,873 A | 10/1993 | Atkinson et al. |
| 5,282,790 A | 2/1994 | Clement |
| 5,295,657 A | 3/1994 | Atkinson |
| 5,295,658 A | 3/1994 | Atkinson et al. |
| 5,300,035 A | 4/1994 | Clement |
| 5,300,036 A | 4/1994 | Mueller et al. |
| 5,306,237 A | 4/1994 | Clement et al. |
| 5,308,336 A | 5/1994 | Hart et al. |

(Continued)

FOREIGN PATENT DOCUMENTS

| | | |
|---|---|---|
| EP | 0066008 A2 | 1/1985 |
| EP | 0131349 A1 | 1/1985 |
| EP | 0617924 A2 | 10/1994 |

*Primary Examiner* — Victoria P Shumate
*Assistant Examiner* — Gerald Landry, II

(57) ABSTRACT

A trocar and cannula assembly with improved conical valve that incorporates a plurality of ribs to restrict and/or otherwise influence valve movement, and a plurality of improved convolutes and bumps to enhance performance characteristics.

19 Claims, 10 Drawing Sheets

U.S. PATENT DOCUMENTS

| | | | |
|---|---|---|---|
| 5,312,351 A | 5/1994 | Gerrone | |
| 5,312,363 A | 5/1994 | Ryan et al. | |
| 5,320,608 A | 6/1994 | Gerrone | |
| 5,334,164 A | 8/1994 | Guy et al. | |
| 5,335,671 A | 8/1994 | Clement | |
| 5,338,392 A | 8/1994 | Clement et al. | |
| 5,342,315 A | 8/1994 | Rowe et al. | |
| 5,344,420 A | 9/1994 | Hilal et al. | |
| 5,350,364 A | 9/1994 | Stephens et al. | |
| 5,360,417 A | 11/1994 | Gravener et al. | |
| 5,366,478 A | 11/1994 | Brinkerhoff et al. | |
| 5,374,244 A | 12/1994 | Clement et al. | |
| 5,376,077 A | 12/1994 | Gomringer | |
| 5,385,553 A | 1/1995 | Hart et al. | |
| 5,389,081 A | 2/1995 | Castro | |
| 5,397,335 A | 3/1995 | Gresl et al. | |
| 5,402,982 A | 4/1995 | Atkinson et al. | |
| 5,407,433 A | 4/1995 | Loomas | |
| 5,409,013 A | 4/1995 | Clement | |
| 5,411,483 A | 5/1995 | Loomas et al. | |
| 5,437,646 A | 8/1995 | Hunt et al. | |
| 5,443,452 A | 8/1995 | Hart et al. | |
| 5,449,141 A | 9/1995 | Gillett et al. | |
| 5,476,475 A | 12/1995 | Gadberry | |
| 5,496,280 A | 3/1996 | Vandenbroek et al. | |
| 5,497,433 A | 3/1996 | Itoh et al. | |
| 5,501,426 A | 3/1996 | Atkinson et al. | |
| 5,505,210 A | 4/1996 | Clement | |
| 5,533,708 A | 7/1996 | Atkinson et al. | |
| 5,542,931 A | 8/1996 | Gravener et al. | |
| 5,549,565 A | 8/1996 | Ryan et al. | |
| 5,569,205 A | 10/1996 | Hart et al. | |
| 5,584,850 A | 12/1996 | Hart et al. | |
| 5,603,702 A * | 2/1997 | Smith et al. | 604/256 |
| 5,628,732 A | 5/1997 | Antoon, Jr. et al. | |
| 5,634,908 A | 6/1997 | Loomas | |
| 5,643,282 A | 7/1997 | Kieturakis | |
| 5,651,771 A | 7/1997 | Tangherlini et al. | |
| 5,657,963 A | 8/1997 | Hinchliffe et al. | |
| 5,662,615 A | 9/1997 | Blake, III | |
| 5,693,031 A | 12/1997 | Ryan et al. | |
| 5,709,664 A | 1/1998 | Vandenbroek et al. | |
| 5,720,730 A | 2/1998 | Blake, III | |
| 5,722,770 A | 3/1998 | Gravener et al. | |
| 5,727,770 A | 3/1998 | Dennis | |
| 5,752,938 A | 5/1998 | Flatland et al. | |
| 5,782,812 A | 7/1998 | Hart et al. | |
| 5,792,112 A | 8/1998 | Hart et al. | |
| 5,792,113 A | 8/1998 | Kramer et al. | |
| 5,797,907 A | 8/1998 | Clement | |
| 5,803,919 A | 9/1998 | Hart et al. | |
| 5,827,228 A | 10/1998 | Rowe | |
| 5,865,807 A | 2/1999 | Blake, III | |
| 5,871,471 A | 2/1999 | Ryan et al. | |
| 5,895,377 A | 4/1999 | Smith et al. | |
| 5,980,493 A | 11/1999 | Smith et al. | |
| 5,984,919 A | 11/1999 | Hilal et al. | |
| 5,989,224 A | 11/1999 | Exline et al. | |
| 6,039,302 A | 3/2000 | Cote, Sr. et al. | |
| RE36,702 E | 5/2000 | Green et al. | |
| D426,635 S | 6/2000 | Haberland et al. | |
| 6,093,176 A * | 7/2000 | Dennis | 604/256 |
| 6,099,505 A | 8/2000 | Ryan et al. | |
| 6,162,196 A | 12/2000 | Hart et al. | |
| 6,193,672 B1 | 2/2001 | Clement | |
| 6,217,555 B1 | 4/2001 | Hart et al. | |
| 6,228,061 B1 | 5/2001 | Flatland et al. | |
| 6,258,065 B1 | 7/2001 | Dennis et al. | |
| D449,887 S | 10/2001 | Haberland et al. | |
| 6,344,038 B1 | 2/2002 | Weber | |
| 6,355,028 B2 | 3/2002 | Castenada et al. | |
| 6,432,085 B1 | 8/2002 | Stellon et al. | |
| 6,482,181 B1 | 11/2002 | Racenet et al. | |
| 6,500,170 B2 | 12/2002 | Palmer et al. | |
| 6,503,245 B2 | 1/2003 | Palmer et al. | |
| 6,551,282 B1 | 4/2003 | Exline et al. | |
| 6,554,823 B2 | 4/2003 | Palmer et al. | |
| 6,569,119 B1 | 5/2003 | Haberland et al. | |
| 6,588,428 B2 | 7/2003 | Shikani et al. | |
| 6,595,946 B1 | 7/2003 | Pasqualucci et al. | |
| 6,612,196 B1 | 9/2003 | Petzold | |
| 6,702,787 B2 | 3/2004 | Racenet et al. | |
| 6,723,073 B2 | 4/2004 | Ley et al. | |
| 6,945,983 B2 | 9/2005 | Dittrich et al. | |
| 6,958,069 B2 | 10/2005 | Shipp et al. | |
| 7,041,055 B2 | 5/2006 | Young et al. | |
| 7,077,865 B2 | 7/2006 | Bao et al. | |
| 7,100,890 B2 | 9/2006 | Core et al. | |
| 7,214,228 B2 | 5/2007 | Crabtree | |
| 7,217,275 B2 | 5/2007 | Crabtree | |
| 7,438,702 B2 * | 10/2008 | Hart et al. | 604/167.03 |
| 2002/0013556 A1 | 1/2002 | Cote et al. | |
| 2003/0216770 A1 | 11/2003 | Persidsky et al. | |
| 2004/0138626 A1 | 7/2004 | Cote et al. | |
| 2004/0171990 A1 * | 9/2004 | Dennis et al. | 604/167.03 |
| 2004/0215107 A1 | 10/2004 | Sarstedt et al. | |
| 2004/0254541 A1 | 12/2004 | Wong et al. | |
| 2005/0033342 A1 | 2/2005 | Hart et al. | |
| 2005/0256461 A1 | 11/2005 | DiFiore et al. | |
| 2006/0025781 A1 | 2/2006 | Young et al. | |
| 2006/0047293 A1 | 3/2006 | Haberland et al. | |
| 2008/0033363 A1 * | 2/2008 | Haberland et al. | 604/167.03 |
| 2010/0004599 A1 * | 1/2010 | Zhou et al. | 604/167.04 |
| 2011/0288483 A1 * | 11/2011 | Zhou et al. | 604/167.03 |

* cited by examiner

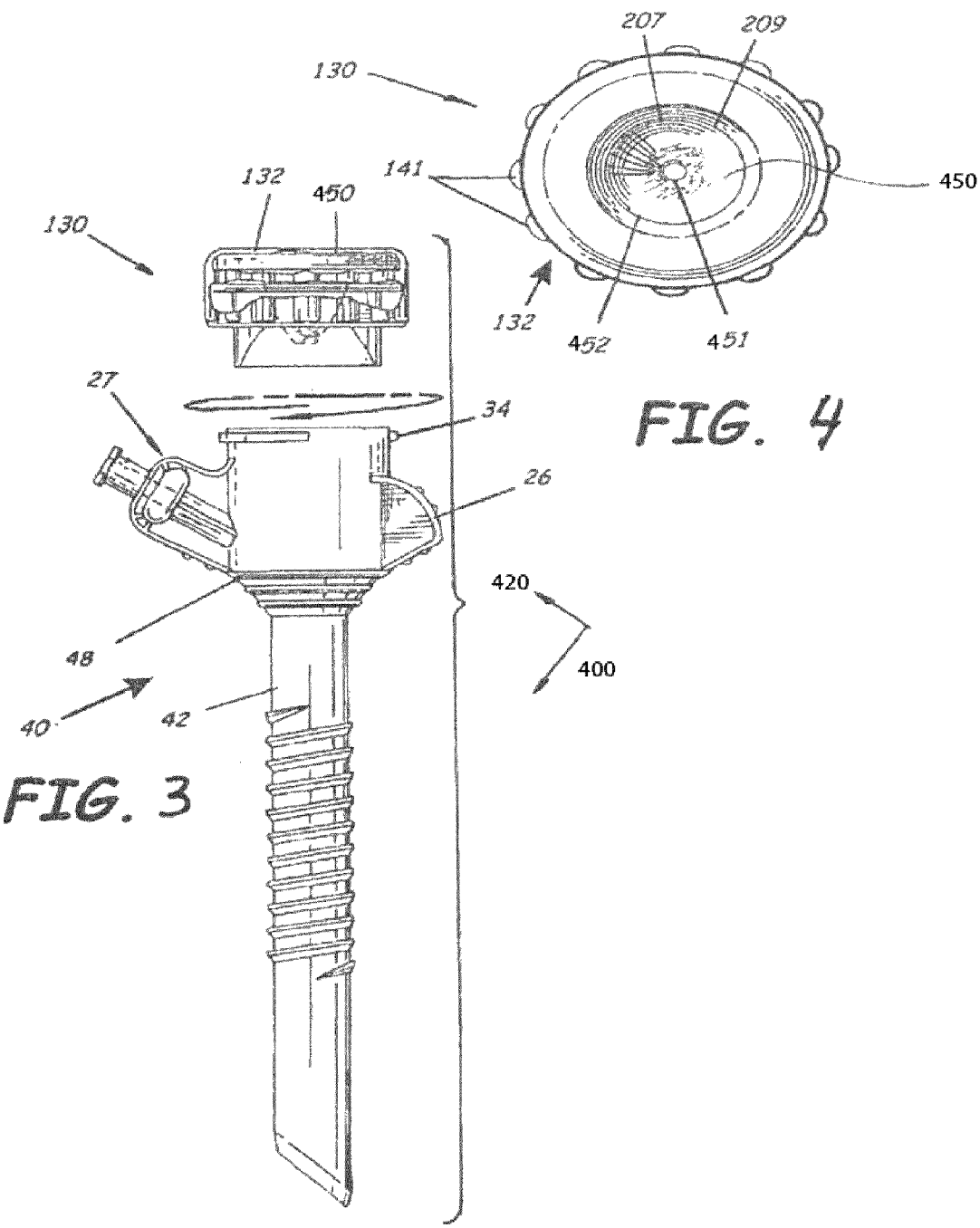

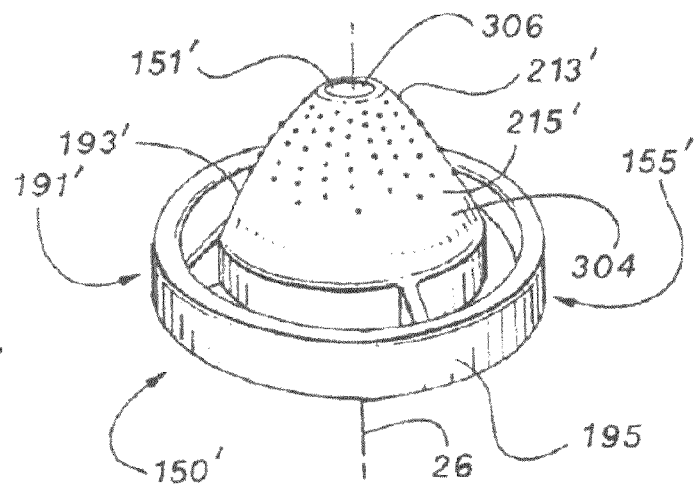
FIG. 7
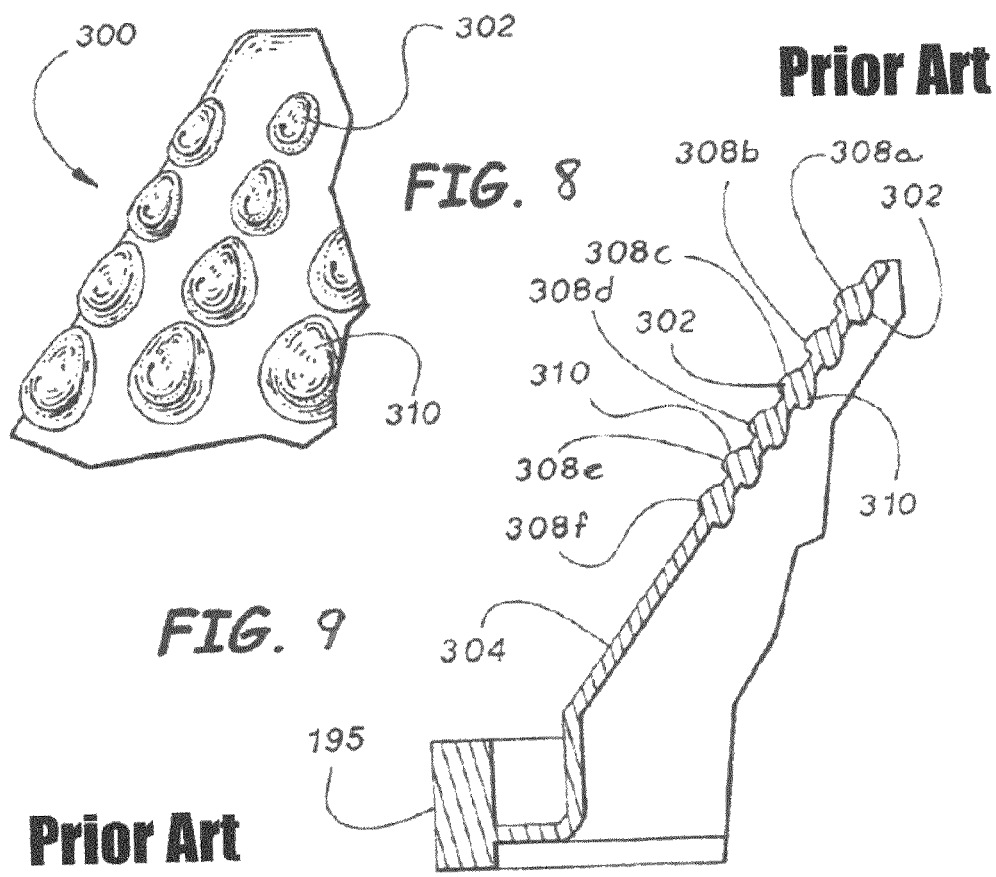
FIG. 8 Prior Art
FIG. 9 Prior Art

TROCAR AND CANNULA ASSEMBLY HAVING IMPROVED CONICAL VALVE, AND METHODS RELATED THERETO

CROSS-REFERENCE AND PRIORITY CLAIM TO RELATED APPLICATION

To the fullest extent permitted by law, the present U.S. Non-Provisional Patent Application claims priority to and the benefit of United States Provisional patent application entitled "Trocar and Cannula Assembly Having Improved Conical Valve, and Methods Related Thereto", filed on Oct. 9, 2009, on behalf of inventor Rogelio A. Insignares, and having assigned Ser. No. 61/250,194, which is fully incorporated herein by reference.

FIELD

The present disclosure relates generally to medical devices, and more particularly to trocar systems, cannulas, valves, and methods related thereto.

BACKGROUND

Numerous trocar systems have been developed for various endoscopic applications in the field of medicine. These trocar systems conventionally include a cannula, through which a trocar or obturator or other endoscopic-related tool extends. In such systems, one or more valves is necessarily positioned within or connected to the proximal end of the cannula. Many such valves are disadvantageously bulky and awkward to use, and complex, multi-component mechanical valves can be difficult and costly to manufacture, and can have increased risk of failure relative to non-mechanical counterparts. Moreover, mechanical valves typically have little or no flexibility.

Valve improvements can serve to enhance handling of trocar systems by medical professionals, facilitating better performance and improving patient surgical experience. Therefore, it is readily apparent that there is a need for an improved conical valve and related trocar and cannula assembly, and methods related thereto, where performance is enhanced, risk of failure is mitigated, and cost-effective production and manufacture is available.

BRIEF SUMMARY

Briefly described, in a preferred embodiment, the present assembly overcomes the above-mentioned disadvantages and meets the recognized need for such a device by providing a trocar and cannula assembly with improved conical valve, and methods related thereto, wherein an improved single-piece valve design allows for easier stretch of the body of the valve, reduces friction, and promotes retention of original shape of the distal center hole, thereby providing improvement, at least in the ability to seal during aggressive manipulation of instruments through the port.

According to its major aspects and broadly stated, in its preferred form, the present system is a trocar and cannula assembly with improved conical valve that incorporates a plurality of ribs to restrict and/or otherwise influence valve movement, and a plurality of improved convolutes and bumps to enhance performance characteristics.

Embodiments of the present invention advantageously provide a valve having a design to provide a secured seal around a plurality of tools that individually and separately extend through the valve, providing for ease of insertion and retraction of various laparoscopic surgical instruments, as well as other surgically-related items with varying diameters, wherein the present system is configured to advantageously accept a broad range thereof. Further, problematical instruments do not get obstructed or caught, such as may occur in some disadvantageous multi-component valve assemblies. Embodiments of the present disclosure also advantageously provide a trocar system having relatively low costs associated with the manufacturing of components of the system, e.g., valves, and thereby reduce the costs associated with the trocar system.

Embodiments of the present disclosure additionally advantageously provide a more flexible trocar system which is effective during various endoscopic surgical procedures. Embodiments of the present invention further advantageously provide enhanced methods of forming a seal around tools and of using a trocar system during surgical procedures.

Embodiments of the present further advantageously provide a valve having peripheries fixedly connected to a valve housing, such that the valve may operate like a membrane, and embodiments of the valve advantageously allow one type of valve, cannula, or trocar system to be readily used for various types and diameters of tools used by medical personnel. Moreover, embodiments of the present disclosure further provide a valve having advantageously improved anti-friction features that facilitate insertion and removal of instruments therethrough. Still further embodiments of the present disclosure may provide for the formation of these anti-friction features according to a new multi-shot liquid silicone rubber process, wherein liquid silicone rubber and traditional thermoplastic elements may be combined in a single molded part. In such an embodiment, for example, plurality of bump features may be molded as a thermoplastic material, with a very low coefficient of friction.

More specifically, the system of the present disclosure in its preferred form is a trocar system comprising a cannula having an elongate cannula body, with medial and distal portions having a first diameter. The cannula body has a proximal portion, connected to the medial portion and opposingly positioned relative to the distal portion, wherein the proximal portion has a second diameter, wherein the second diameter is greater than the first diameter. According to a preferred embodiment of the trocar system, a valve housing is detachably connected to the proximal portion of the cannula body, with an axis and first opening at a proximal end of the valve housing, a second opening at a distal end of the valve housing, and an axially downward facing shoulder. The first opening of the valve housing is preferably defined by a plurality of sidewalls extending in a substantially axial direction, and has a first opening diameter.

According to embodiments of the present disclosure, the trocar system also includes a cap assembly which includes at least one valve positioned within the valve housing. According to an embodiment of the cap assembly, the at least one valve can include a valve body having an annular-shaped valve opening adapted to individually and separately receive a plurality of different elongate tools. Each of the tools have a different diameter therethrough so that when any one of the plurality of elongate tools is positioned through the valve opening, a septum seal is maintained between peripheries of the valve body surrounding the valve opening and abuttingly contacting outer peripheries of the any one of the plurality of elongate tools extending therethrough.

The valve body preferably has a periphery valve section connected to and extending radially outwardly from peripheries of the valve body. The periphery valve section includes an outer ring with an outer perimeter thereof defining an outer perimeter of the septum valve, the outer ring engaging the axially downward facing shoulder of the valve housing, and convolutes defined between the outer ring and the valve body. The periphery valve section also has a plurality of rib members, each radially extending at least a portion of the distance between an outer perimeter of the valve body and the outer perimeter of the periphery valve section, and symmetrically positioned spaced-apart from each other. The periphery valve section may have a greater flexibility than the valve body.

The trocar system also preferably includes a compression ring positioned in the valve housing adjacent the septum valve. The compression ring compresses the outer ring of the septum valve against the axially downward facing shoulder of the valve housing in order to fixedly position the septum valve within the valve housing. The compression ring has a compression ring opening substantially aligned with the first opening of the valve housing. The trocar system further comprises a plurality of tools that each have an elongate body for extending through the valve housing, the valve opening, and the cannula.

Further, more particularly and preferably, the cap assembly of the trocar system may include, but is not limited to, a valve housing having at least one opening formed in line with an axis of the valve housing, with the at least one opening being defined by a plurality of sidewalls extending in a substantially axial direction. The cap assembly also may include at least one valve positioned adjacent to the at least one opening of the valve housing. The at least one valve includes a valve body having an annular-shaped valve opening adapted to individually and separately receive a plurality of different elongate tools. Each of the elongate tools can have a different diameter so that when any one of the plurality of elongate tools is positioned through the valve opening, and when the valve is abuttingly contacting outer peripheries of any one of the plurality of diameter elongate tools extending therethrough, a septum seal is maintained between peripheries of the valve body surrounding the valve opening. The valve body also has a periphery valve section connected to and extending radially outwardly from peripheries of the valve body. The periphery valve section has one or more convolutes within the periphery valve section. The periphery valve section also has a plurality of rib members radially extending at least a portion of the distance between an outer perimeter of the valve body and an outer perimeter of the periphery valve section, and may have a circumferential baffle defined between the plurality of convolutes and the inner perimeter of the outer ring.

According to another embodiment of the trocar system, the system may include a valve housing adapted to detachably connect to a cannula and characterized by having a proximal end housing portion, a distal end housing portion, and a medial housing portion connected therebetween having a proximal valve housing inner perimeter surface and a distal valve housing inner perimeter surface which can be of the same or different diameters. The proximal end housing portion can include a first opening having a first opening diameter defined by portions of an inner valve housing sidewall extending distally in a substantially axial direction. The proximal end housing portion can also include an annular valve ring recess adapted to receive an annular valve ring which surrounds the first opening. The distal end housing portion can include a second opening diameter defined by a distal valve housing sidewall extending in a substantially axial direction.

According to an another embodiment of the cap assembly, the at least one valve positioned within a valve housing may include a first valve having a valve body which includes a proximal valve section fixedly positioned within the valve housing and a distal valve section extending axially from the proximal valve section and into the proximal portion of the cannula. The proximal valve section can include a valve ring positioned in the valve ring recess of the valve housing. The valve ring has a proximal surface, a distal surface, an inner perimeter surface, and an outer perimeter surface defining an outer perimeter of the valve body.

The proximal surface and the distal surface of the periphery valve section are each preferably further defined by two sub-element surfaces, wherein the first sub-element surface of the proximal surface is defined in a first plane and proximate the inner perimeter of the periphery valve section, and the second sub-element surface of the proximal surface is defined in a second plane and proximate the outer perimeter of the periphery valve section. A similar relationship exists between the two sub-element surfaces of the distal surface of the periphery valve section, wherein the first sub-element surface of the distal surface is defined in a first plane and proximate the inner perimeter of the periphery valve section, and the second sub-element surface of the distal surface is defined in a second plane and proximate the outer perimeter of the periphery valve section. Accordingly, neither the proximal surface of the periphery valve section nor the distal surface of the periphery valve section is flat.

The periphery valve section may include a circumferential baffle element related to the proximal valve section of the valve body, wherein the circumferential baffle element may preferably be defined in the second plane proximate the outer perimeter of the periphery valve section. The proximal valve section of the valve body can also include a plurality of convolutes, each preferably having a first sidewall extending radially inwardly from a portion of the circumferential baffle and a second sidewall extending axially from the first sidewall substantially parallel to the inner perimeter surface of the valve ring and forming an inner radial periphery of the proximal valve section.

The inner perimeter surface of the periphery valve section, the first sidewall, and the second sidewall of each of the plurality of convolutes preferably form a respective convolute recess for each of the plurality of convolutes. The proximal valve section of the valve body can also include a plurality of rib members, each radially extending at least a portion of the distance between the inner radial periphery of the proximal valve section and inner perimeter surface of the valve ring and can be symmetrically positioned spaced-apart from each other. Preferably, each of the plurality of rib members extends radially from the inner radial periphery of the proximal valve section to the circumferential baffle element, wherein the circumferential baffle element extends radially from the plurality of convolutes to the inner perimeter surface of the valve ring.

The distal valve section of the valve body can include a valve extension extending axially from the plurality of convolutes. The valve extension can include a proximal end portion substantially connected to a distal portion of each of the plurality of convolutes, a distal end portion, and a substantially conically shaped medial portion connected to and extending therebetween. An annular-shaped valve opening is positioned in the distal end portion of the valve extension and is adapted to individually and separately receive therethrough any one of a plurality of different elongate tools, each having a different diameter so that when any one of the plurality of elongate tools is positioned through the valve opening, a seal, e.g., septum seal, is maintained between peripheries of the valve extension surrounding the valve opening and outer peripheries of any one of the plurality of elongate tools extending therethrough.

The first valve may also include a compression ring positioned in the valve housing abuttingly contacting an axially facing distal surface of the valve ring to hold the valve ring in the valve ring recess and to compress the valve ring against an axially facing inner surface of the proximal end housing portion of the valve housing adjacent the valve ring recess in order to fixedly position the valve within the valve housing. The compression ring may include a compression ring opening substantially aligned axially with the first opening of the valve housing to allow extension of the plurality of elongate tools therethrough, an outer perimeter surface having a radial diameter sized so that the compression ring substantially abuttingly contacts the distal valve housing inner perimeter surface when positioned within the valve housing, and an annular flange extending into each one of the plurality of convolute recesses to individually and separately engage a corresponding one of the plurality of convolutes to further enhance positioning and securing of the first valve within the valve housing.

The cap assembly can also include a second valve to advantageously help ensure inter-cavity sealing. The second valve can include an annular flange portion spaced axially from the valve ring of the first valve and having a radial diameter sized so that the annular flange portion substantially abuttingly contacts both the distal valve inner housing perimeter surface and an axially facing distal surface of the compression ring adjacent the compression ring opening to enhance positioning of the second valve at least partially within the valve housing. The second valve can also have a second valve opening positioned within the annular flange portion and substantially aligned axially with the first opening of the valve housing to allow extension of the plurality of elongate tools therethrough, an annular-shaped sidewall connected to the annular flange and extending distally in a substantially axial direction when positioned in the valve housing, and a pair of valve flaps connected to and extending inwardly from the annular-shaped sidewall and having at least one slit along common peripheral edges thereof through which the plurality of tools extend individually and separately. The second valve can be held in place through use of a cap seal ring positioned at least partially within the valve housing and positioned to abuttingly contact a distal surface of the annular flange portion of the second valve when the second valve is positioned in the valve housing. The cap seal ring can have an axially extending annular-shaped flange axially spaced apart from the compression ring to provide a slot or recess to releasably receive the annular flange portion of the second valve. The cap seal ring can also include a plurality of radially extending flanges each adapted to engage other peripheries of a separate one of the plurality of radially extending flanges of the cannula to slidably detachably connect the valve housing to the cannula.

Embodiments of the present disclosure also preferably include methods of using a trocar system. For example, one method embodiment may include the step of providing a cap assembly in a trocar system. The cap assembly has a septum valve including a valve body having an annular-shaped valve opening positioned in a medial portion of the valve body adapted to receive individually and separate a plurality of tools therethrough so that when any one of the plurality of tools is positioned through the valve opening abuttingly contacting outer peripheries of the any one of the plurality of tools extending therethrough, a septum seal is maintained between peripheries of the valve body surrounding the valve opening. The valve body can include a periphery valve section connected to and extending radially outwardly from peripheries of the valve body and having an outer perimeter thereof adapted to be fixedly connected to the valve housing. The periphery valve section can also have a plurality of rib members each radially extending at least a portion of the distance between an outer perimeter of the valve body and the outer perimeter of the periphery valve section and symmetrically positioned spaced-apart from each other. The periphery valve section can also have a circumferential baffle member defined proximate the outer perimeter of the periphery valve section, wherein the plurality of rib members preferably extend between the outer perimeter of the valve body and the circumferential baffle member. The periphery valve section can have a greater flexibility than the valve body.

The method of using a trocar system can also include the step of inserting a tool through the septum valve and cap assembly comprising the septum valve thereof. During the inserting step, the periphery valve section may be deformed temporarily so that the valve body extends distally by contact pressure from the tool and so that a distal end of the tool is guided toward the valve opening and then the periphery valve section is refracted to its selected biased position upon the complete insertion of the tool. The method of using a trocar system can also include the step of guiding the tool to the septum valve with a substantially cylindrical-shaped cap assembly opening when the tool is being inserted through the cap assembly. The method of using a trocar system can further include the steps of extending the tool through a cannula body matingly connected to the cap assembly at a proximal portion thereof, detaching the cap assembly from the proximal portion of the cannula body, and removing tissue or other specimen from the cannula body.

According to another embodiment of the method of using a trocar system, the method can include the step of providing a cap assembly in a trocar system including a valve positioned at least partially within a valve housing. The valve can include a valve body having a proximal valve section positioned within the valve housing and a distal valve section extending axially from the proximal valve section and including a valve extension having a proximal end portion, a distal end portion, and a substantially conically shaped medial portion connect to and extending therebetween. A valve opening is positioned in the distal end portion of the valve extension and is adapted to individually and separately receive therethrough any one of a plurality of different elongate tools. The method can also include the step of inserting a tool through the cap assembly including the valve extension and a valve opening thereof, during which the valve extension guides the distal end of the tool to the valve opening and upon reaching the valve opening, the valve opening is deformed temporarily by contact pressure from the tool so that upon the complete insertion of the tool, a seal is formed around outer peripheries of the tool. The method further includes the steps of guiding the tool to the valve extension with a substantially cylindrical-shaped cap assembly opening when the tool is being inserted through the cap assembly, extending the tool through a cannula body matingly connected to the cap assembly at a proximal portion thereof, detaching the cap assembly from the proximal portion of the cannula body, and removing tissue or other specimen from the cannula body.

The valve also preferably includes a plurality of closely and symmetrically spaced friction-reduction features to advantageously minimize electrostatic forces between instruments and the valve. A reduction in electrostatic adhesion can be realized from the friction-reduction features, preferably protrusions formed on the inner and outer surfaces of the conically shaped medial portion, proximate the distal end and the valve opening. Preferably, a first circumferential row of protrusions is defined proximate the valve opening in a closely-spaced conformation, whereafter a second circumferential row of protrusions is defined in a position of greater distance relative to the valve opening, wherein the same total number of protrusions is preferably defined in the second row as the first row, but given the increased diameter of the conical valve at the location of the second row relative to that of the first row, the second row protrusions are less closely-spaced. Thereafter, further rows are defined in similar fashion. The positioning of the protrusions of each adjacent circumferential row may also be juxtaposed, such that a radial twist pattern may be defined by the protrusions about the conical valve proximate the distal end and the valve opening. The friction-reduction features essentially serve to create a gap between an instrument surface and a flat area of the valve, beneficially decreasing the total area of contact in the trocar system otherwise potentially faced with a relatively large surface of contact area, high pressure contact, and high shear stress deformation. The protrusions thus function to reduce undesirable pressure contact between the instrument and the valve. Moreover, as noted hereinabove, embodiments wherein the protrusions may be formed from a thermoplastic material with a low coefficient of friction may serve to limit frictional forces even further by effectively changing the coefficient of friction acting on the entire valve system.

A further improvement proximate the distal end of the valve relates to the definition of the plurality of friction-reduction features definition on both a distal surface and a proximal surface of the distal end of the valve, wherein each protrusion preferably forms a cone, wherein the shape and placement of friction-reduction features enhances friction reduction. That is, kinetic friction between the valve and related instruments is advantageously minimized as the valve opening is deformed temporarily by contact pressure from the tool, wherein contact area between the valve and the instruments is reduced. Moreover, elongation or other reactive force redirection by the circumferential baffle element serves to minimize deformation of the valve opening as well. The friction-reduction features, especially with the circumferential baffle, can reduce the resistive forces between the contact surfaces of an inserted instrument and the valve without compromise to the septum seal or to the inherent flexibility and adaptability of the valve of the present invention, wherein a broad endoscopic instrument diameter range, from about 5 mm to 15 mm diameter, can be successfully accepted. The friction-reduction features, both the plurality of protrusions, or cones, are preferably defined proximate the apical end of the valve, in anticipation of contact with the plurality of elongate tools extended therethrough, and are further preferably defined on both opposing surfaces in order that advantageous minimization of electrostatic forces may be realized also during contact between the valve body and the second valve. Again, these friction-reduction features may be formed from material with a low coefficient of friction relative to the material of the valve body, such as a thermoplastic, wherein further friction-reduction benefits may be realized.

Embodiments of the present invention also include methods of forming a valve for a trocar system. For example, a method of forming a valve for a trocar system can include first inserting a valve having a valve body into the valve housing. A compression ring, for example, coated with an ultraviolet bonding agent, is then placed into the valve housing adjacent and abuttingly contacting the valve in a "stacked" fashion. Following this, the second valve is inserted into the valve housing adjacent and abuttingly contacting the compression ring, and a cap seal ring coated with an ultraviolet bonding agent is placed into the valve housing abuttingly contacting outer peripheries of the second valve. Both the compression ring and cap seal ring can be coated with an ultraviolet bonding agent, along with the outer peripheries thereof abuttingly contacting the inner peripheries of the valve housing. Once each of the components is in its place, the entire cap assembly is placed in a compression system, wherein each component is compressed to its desired depth into the valve housing. At that point, an ultraviolet light is exposed to the ultraviolet bonding agent to cure the materials. Upon the completion of the curing, the cap assembly is formed as one unit. Beneficially, the second valve can be readily removed and exchanged for a replacement.

When constructing a trocar system, the cap assembly is abuttingly and releasably connected to a cannula. The proximal end portion of the cannula body has at least one valve housing mating portion associated therewith, and the cap seal ring positioned in the valve housing also has at least one cannula body mating portion or flange associated therewith so that the cap assembly matingly attaches to the cannula body in a secured position and whereby movement of the cap assembly, e.g., rotation, by a hand of a user, releases, e.g., unsecures or unlocks, the respective mating portions for ready removal of the cap assembly by the user with the valve and second valve and so that specimens, e.g., tissue, can be readily removed from the cannula body without damage by the first and second valve. Advantageously, the extraction of large tissue samples and/or gauze packs can be accomplished without removing the cannula from the area where various endoscopic procedures take place.

These and other features and advantages of the present system and methods related thereto will become more apparent to one skilled in the art from the following description and claims when read in light of the accompanying drawings.

BRIEF DESCRIPTION OF THE DRAWINGS

The present disclosure will be better understood by reading the Detailed Description of the Preferred and Alternate Embodiments with reference to the accompanying drawing figures, in which like reference numerals denote similar structure and refer to like elements throughout, and in which:

FIG. 3 is a side elevational view of a trocar system according to an embodiment of the present disclosure;

FIG. 4 is a top plan view of a cap assembly of a trocar system according to an embodiment of the present disclosure;

FIG. 7 is a perspective view of a valve of a trocar system according to a prior art embodiment;

FIG. 8 is a magnified, cut-away surface view of a valve of a trocar system according to a prior art embodiment;

FIG. 9 is a cross-sectional, cut-away view, taken along line 26-26 of the valve of FIG. 7, according to a prior art embodiment;

DETAILED DESCRIPTION OF THE PREFERRED AND ALTERNATE EMBODIMENTS

Figure 1:
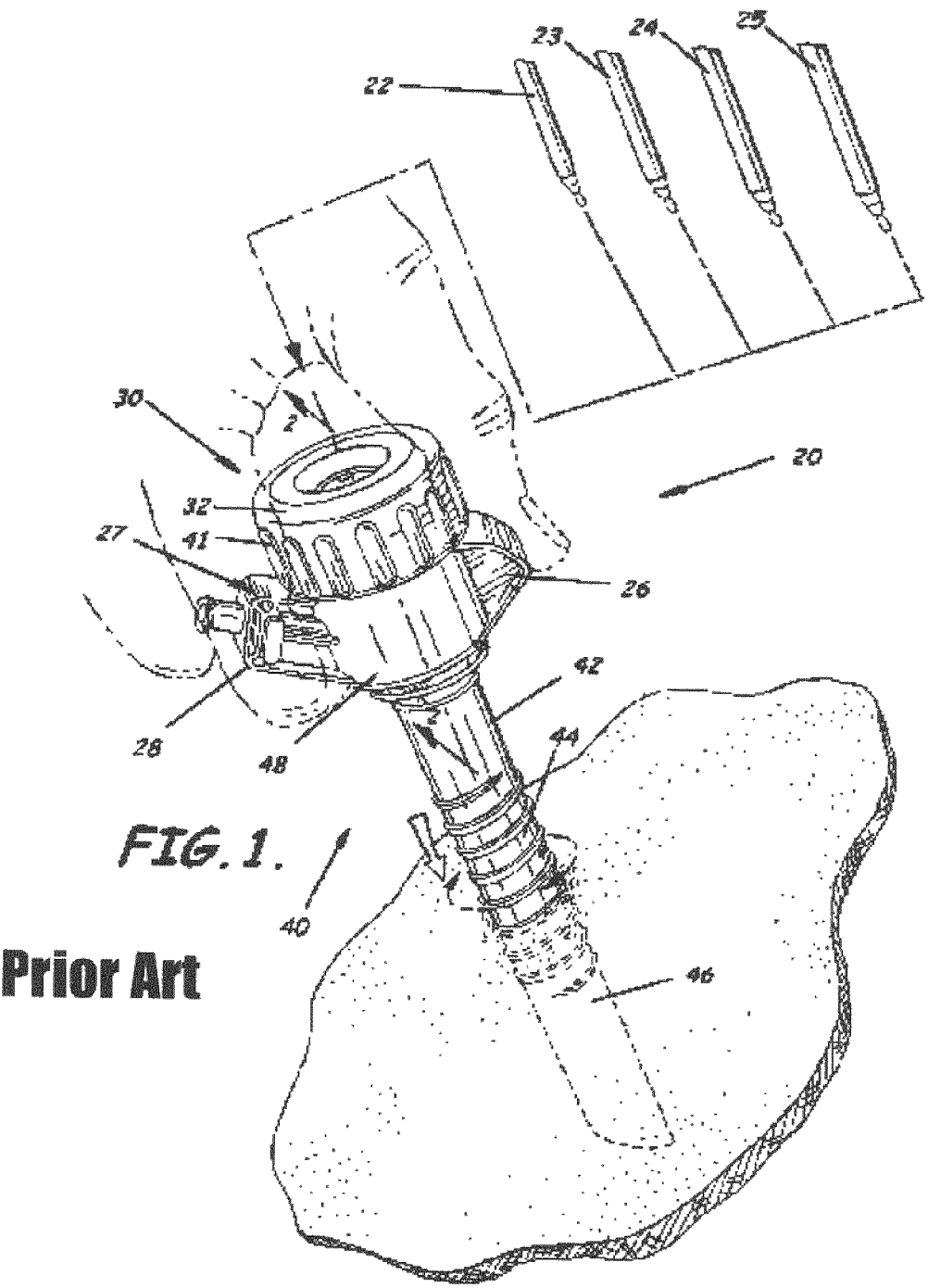
FIG. 1 is a perspective environmental view of a trocar system positioned within a layer of epidermis of a patient, according to a prior art embodiment.

In describing the preferred and alternate embodiments of the present invention, as illustrated in the figures and/or described herein, specific terminology is employed for the sake of clarity. The invention, however, is not intended to be limited to the specific terminology so selected, and it is to be understood that each specific element includes all technical equivalents that operate in a similar manner to accomplish similar functions.

Referring now to FIGS. 1-2 and 5-9, it is instructive to reference prior art embodiments, as previously disclosed in commonly-owned U.S. patent application Ser. No. 11/503,314 and U.S. patent application Ser. No. 11/807,202, wherein the presently disclosed trocar and cannula assembly 400 having improved conical valve 450 may include one or more features in common therewith. That is, prior art nonplanar valves 150 and 150' are first referenced and instructively described relative to use with cannula 40 and common features of cap assembly 130 shared with prior trocar system 120 and the presently disclosed trocar system 420. Thereafter, embodiments of improved conical valve 450 are described, with preferred particularity.

In general, improved conical valve 450 and nonplanar valves 150 and 150' may each be used with cannula 40. Cap assembly 130 of prior art trocar system 120, as well as of presently disclosed trocar system 420, preferably comprises valve housing 132, wherein valve housing 132 may have, for example, a substantially annular shape, with proximal end housing portion 171, distal end housing portion 173, and medial housing portion 175. Proximal end housing portion 171 preferably includes first opening 131 having a first opening diameter defined by portions of inner valve housing sidewall 177 and extending distally in a substantially axial direction. Inner valve housing sidewall 177, forming first opening 131, extends substantially axially downward toward a valve opening, referenced prior art valve opening 151, 151' of prior art valve 150, 150', respectively, or valve opening 451 of improved conical valve 450. The upper portion of the first opening 131 can be rounded so as not to have any right angle edges at the first opening 131, but with the resulting cross-section forming a substantially cylindrical first opening 131 extending along the same axis as that for the prior art valve opening 151, 151' or improved conical valve opening 451. The proximal end housing portion 171 can also include an annular valve ring recess 179 for retaining the prior art valve 150, 150' or improved conical valve 450. The distal end housing portion 173 can include a second opening 133 having a second opening diameter defined by a distal valve housing sidewall 181 extending in a substantially axial direction. The medial housing portion 175 can includes a first proximal valve housing inner perimeter surface 183 and a second distal valve housing inner perimeter surface 185 which can have a perimeter size or circumference the same or slightly larger than that of the first proximal valve housing inner perimeter surface 183.

Cap assembly 130 may also include compression ring 136 positioned in valve housing 132 at a medially axial position between first and second openings 131, 133 of valve housing 132, abuttingly contacting axially facing distal surface 199 of valve ring 195. Compression ring 136 includes compression ring opening 137, substantially aligned axially with first opening 131 of valve housing 132 to allow extension of the plurality of elongate tools therethrough. Compression ring opening 137 can also be sized to allow at least portions of inner valve housing sidewall 177 and valve 150, 150' or 450 to extend therethrough. Compression ring 136 also includes outer perimeter surface 217 having a radial diameter sized so that compression ring 136 substantially abuttingly contacts proximal valve housing inner perimeter surface 183 when positioned within valve housing 132 and includes annular flange 219 extending preferably into each one of the plurality of convolute recesses 411.

Compression ring 136 is positioned to compress valve ring 195, 195' or 495 against an axially facing inner surface and an axially facing shoulder of proximal end housing portion 171 of valve housing 132 which together, along with a portion of first proximal valve housing inner perimeter surface 183 of medial housing portion 175, form valve ring recess 179 and/or compress the valve ring 195 against first proximal valve housing inner perimeter surface 183 of medial housing portion 175, to hold valve ring 195 in valve ring recess 179 to fixedly position the valve 150, 150' or 450 within valve housing 132. That is, compression ring 136 is positioned so that proximal valve housing inner perimeter surface 183, surfaces forming valve ring recess 179, and annular flange 219 of compression ring 136 rigidly hold valve ring 195, 195' or 495 within valve housing 132.

Annular flange 219 of compression ring 136 can include a plurality of notches 221 symmetrically positioned spaced-apart from each other so that each of the notches 221 aligns with and receives a separate one of the plurality of rib members 459 to thereby rotationally align the compression ring 136 with the valve ring 495 when positioned in contact therewith. Alternatively, the annular flange 219 can include a plurality of separate spaced apart flanges (not shown) having a gap between each pair of flanges defining the notch 221 and aligned with the plurality of rib members 459 to thereby enhance positioning of the valve ring 195. To further enhance positioning of the valve ring 195, according to an embodiment of the valve housing 132 and valve ring 195, the axially facing inner surface of the proximal end housing portion 171 of the valve housing 132 can include one or more protuberances 205 extending at least partially along the length of the valve ring recess 179, and the proximal surface 197 of the valve ring 195 can include one or more recesses 206 or can deform to form a recess 206, as illustrated, to receive the one or more protuberances 205 to thereby enhance positioning of the valve ring 195 within the valve housing 132.

Cap assembly 130 can also include second valve 160. Second valve 160 is advantageously positioned adjacent second opening 133 of valve housing 132, abuttingly contacting compression ring 139. Second valve 160 advantageously has annular flange portion 162 spaced axially from the valve ring of the first valve 150, 150' or 450. Annular flange portion 162 can have a radial diameter sized so that annular flange portion 162 substantially abuttingly contacts the distal valve inner housing perimeter surface 185 and axially facing distal surface of compression ring 136 adjacent compression ring opening 137 to enhance the positioning of second valve 160 within valve housing 132. Second valve 160 includes second valve opening 223 positioned within annular flange portion 162 and, when positioned within valve housing 132, is substantially aligned axially with first and second openings 131, 133, of valve housing 132 to allow extension of the plurality of elongate tools therethrough.

Annular-shaped sidewalls 164 are connected to annular flange portion 162 and extend distally in a substantially axial direction when positioned in valve housing 132. At least one pair of valve flaps 166 is connected to and extends inwardly from sidewalls 164 and flange portion 162. Sidewalls 164, for example, can extend distally of the end of valve housing 132 so that flange portion 162 retains only portions of second valve 160 within valve housing 132 and yet slidably or in a spaced-apart relation have other portions which are positioned within proximal portion 48 of cannula body 42. Similarly, portions of the valve extension 452 and/or the valve opening 451 of the first valve 450 can extend within the proximal portion 48 of the cannula body 42. The pair of valve flaps 166 has at least one opening or slit 168 along common peripheral edges thereof through which the tools 22, 23, 24, 25, can individually and separately extend. Second valve 160 also advantageously can have ribs or rib members (not shown), e.g., formed integrally therewith as a single piece, and connected to sidewalls 164 to reduce drag as will be understood by those skilled in the art. Second valve 160 can also be advantageously impregnated with a lubricant such as an oil material to enhance performance thereof. It should be noted that the illustrated sidewalls 164 can be replaced with other forms of extension extending from annular flange portion 162 of second valve 160. Further, valve opening 168 can take other forms, such as an annular shaped opening or other known to those skilled in the art.

Second valve 160, in general, and the portion of sidewalls 164 surrounding opening 168, in particular, can be formed of a flexible material similar to that used in forming the first valve 450. For example, the flexible material advantageously can include a silicon material coated in paralene to enhance the strength of valve 160 and to enhance sliding and/or sealing of the plurality of tools.

In order to enhance positioning of second valve 160, a proximal surface of annular flange portion 162 of second valve 160 can include an at least partially annular recess 227 or can deform to form recess 227, as illustrated, to receive an at least partially annular protuberance 225 extending from a distal surface of compression ring 136 to thereby enhance positioning of second valve 160 at least partially within valve housing 132.

A distal surface of annular flange portion 162 of second valve 160 can further include a second valve annular-shaped recess 229 adapted to receive an axially extending annular-shaped flange 272 of proximal portion 48 of cannula 40 to thereby enhance positioning of at least part of proximal portion 48 of cannula 40 within valve housing 132.

Cap assembly 130 can also include cap seal ring 138 positioned at least partially within valve housing 132 and having an axially extending flange 274 positioned to abuttingly contact a distal surface of annular flange portion 162 of second valve 160 when positioned in valve housing 132. Cap seal ring 138 can include a plurality of radially extending flanges 135, each adapted to engage outer peripheries of a separate one of the plurality of radially extending flanges 34 of cannula 40 to slidably detachably connect valve housing 132 to cannula 40. Cannula 40 can also include an annular shaped axially extending flange adapted to engage annular-shaped recess 229 of second valve 160 to thereby enhance positioning of cannula 40 securely against second valve 160 when positioned in engagement with radially extending flanges 135 of cap seal ring 138.

Figure 6:
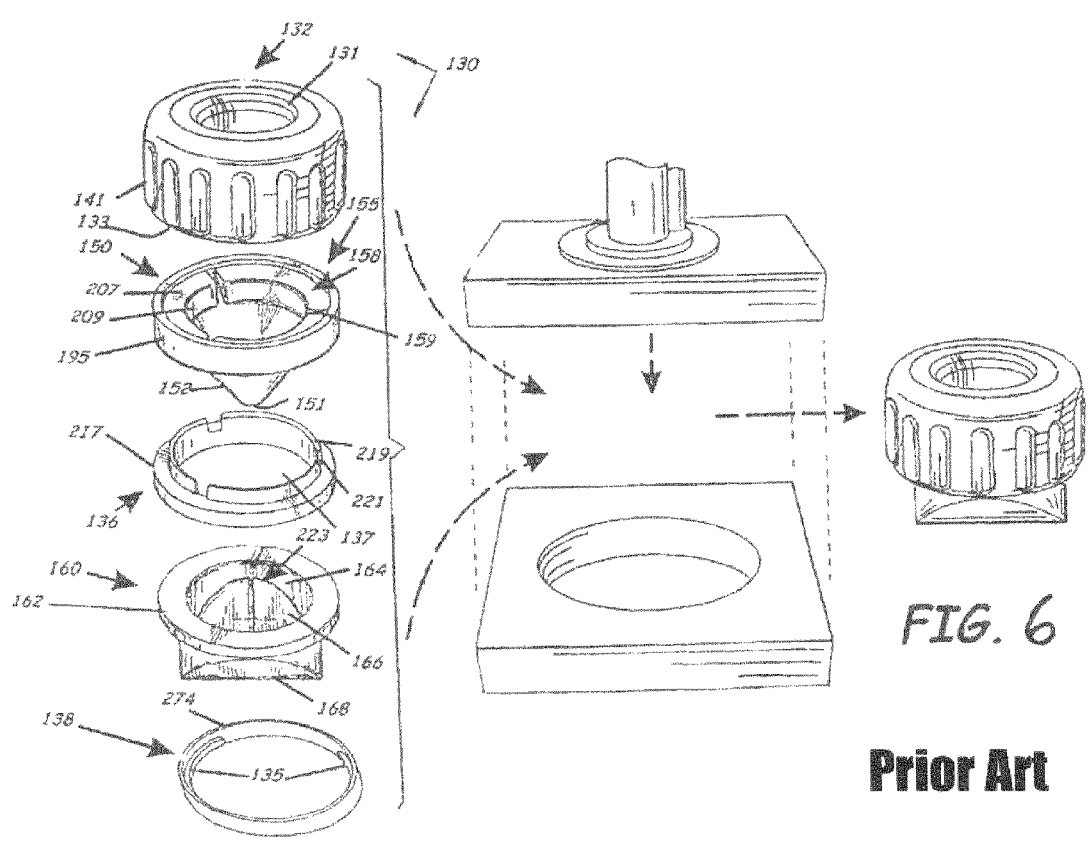
FIG. 6 is an environmental perspective view of a valve, valve mold, and a slab illustrating the formation of a valve according to a prior art embodiment.

Improved conical valve 450, as with prior art valve 150, 150', is advantageously fixedly secured to valve housing 132. FIG. 6 illustrates an exemplary construction process of a prior art cap assembly 130, as instructive of the similar construction process of the presently disclosed cap assembly 430. To provide secure sealing, prior art valve 150 (or similarly improved conical valve 450, as may be so read throughout this and the immediately following exemplary cap assembly construction process paragraphs) is first inserted into valve housing 132. Then compression ring 136, for example, coated with an ultraviolet bonding agent, is placed into valve housing 132 adjacent and abuttingly contacting valve 150 in a "stacked" fashion. Following this, second valve 160 is inserted into valve housing 132 adjacent and abuttingly contacting compression ring 136, and cap seal ring 138 coated with an ultraviolet bonding agent is placed into valve housing 132 and abuttingly contacting outer peripheries of second valve 160. Both compression ring 136 and cap seal ring 138 can be coated with an ultraviolet bonding agent along the outer peripheries thereof abuttingly contacting the inner peripheries of valve housing 132.

Once each of the components is in its place, the entire cap assembly is placed in a compression system, wherein each component is compressed to its desired depth into valve housing 132. At that point, an ultraviolet light is exposed to the ultraviolet bonding agent to cure the materials. The curing takes place in about 8 seconds. Upon the completion of the curing, cap assembly 130 is formed as one unit. Beneficially, second valve 160 can be readily removed and exchanged for a replacement.

When constructing a trocar system 120, cap assembly 130 is then abuttingly connected to cannula 40. Proximal end portion 48 of cannula body 42 has at least one valve housing mating portion 34 associated therewith and cap seal ring 138 positioned in valve housing 132 also has at least one cannula body mating portion or flange 135 associated therewith so that cap assembly 130 matingly attaches to cannula body 42 in a secured position and whereby movement of cap assembly 130, e.g., rotation, by a hand of a user releases, e.g., unsecures or unlocks, the respective mating portions 34, 135 for ready removal of cap assembly 130 by the user with the first and second valves 450, 160, and so that specimens, e.g., tissue, can be readily removed from cannula body 42 without damage by the first and second valves 450, 160. The extraction of large tissue samples and/or gauze packs can be accomplished without removing cannula 40 from the area where various endoscopic procedures take place.

Figure 2:
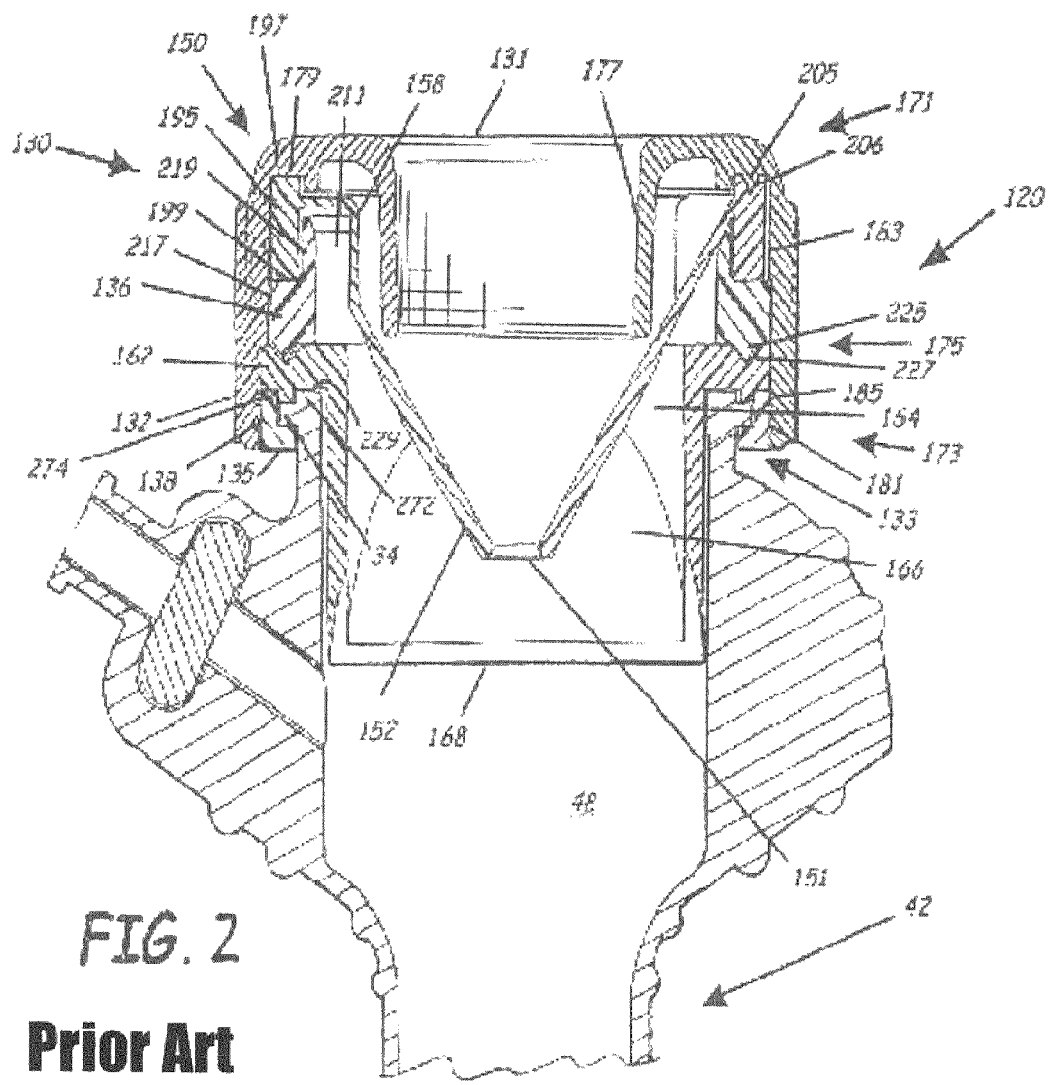
FIG. 2 is a fragmentary sectional view of a trocar system having first and second valves, according to a prior art embodiment.
Figure 5:
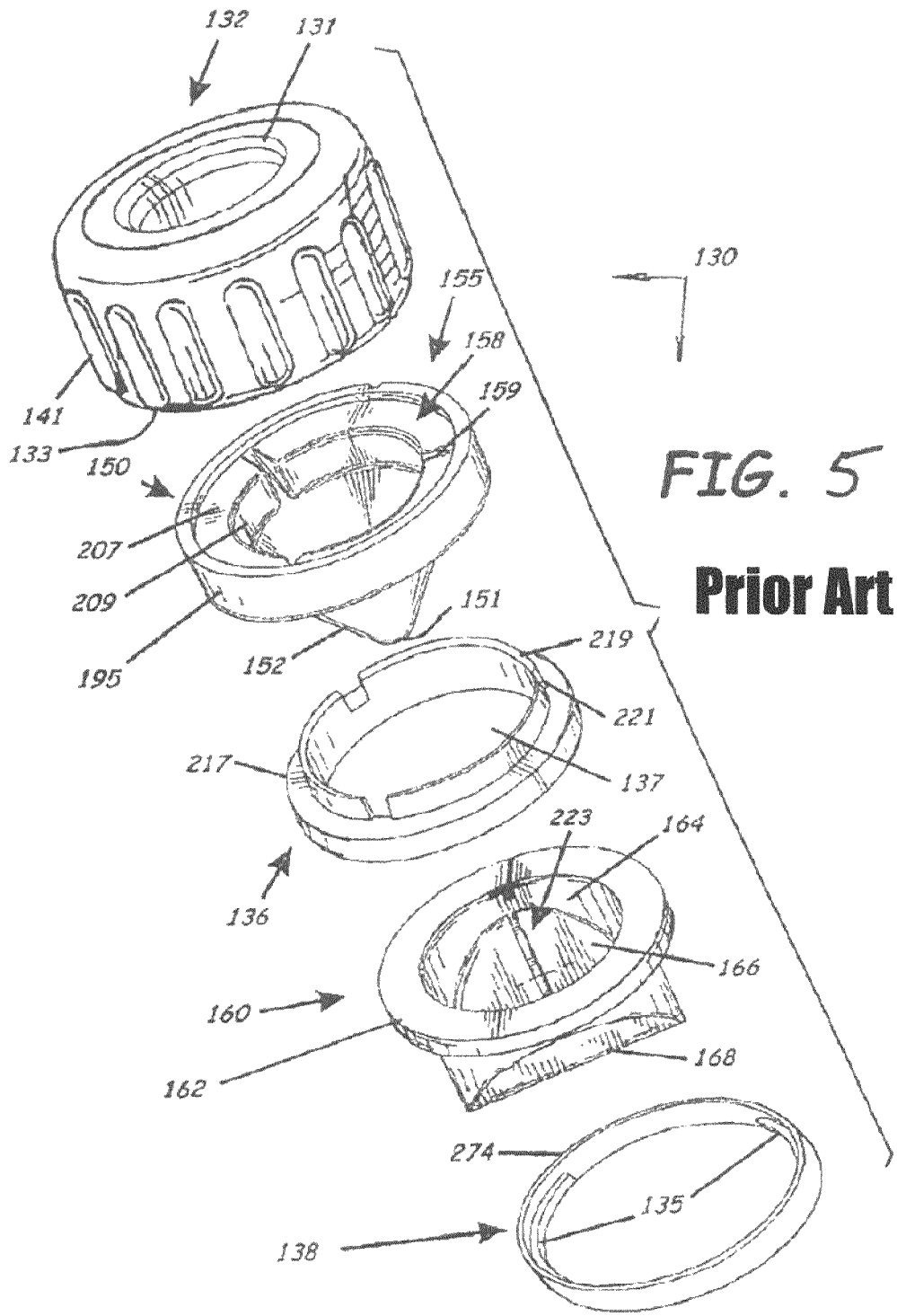
FIG. 5 is an exploded view of a cap assembly of a trocar system according to a prior art embodiment.

As perhaps best shown in FIGS. 2 and 5, the prior art valve 150, 151', as with improved conical valve 450', can include valve body 155, 155' or 455, respectively, positioned at least partially within valve housing 132, axially aligned with the first opening 131 of the valve housing 132. Valve body 155, 155' or 455 includes proximal valve section 191, 191' or 491, respectively, fixedly positioned entirely within valve housing 132, and distal valve section 193, 193' or 493 extending axially from proximal valve section 191, 191' or 491. These common general features relative to prior art valve 150, 150' and improved conical valve 450 are related to facilitate general understanding relative to common interaction within cap assembly 40, but should not be understood to indicate similarity of specific structure or performance between prior art valve 150, 150' and improved conical valve 450, or to impart any limitation to the presently disclosed improved conical valve 450 other than as specifically described herein.

Valve 450 has periphery valve section 456 connected to and extending radially outwardly from peripheries of the base of valve extension 452. Periphery valve section 456 includes valve ring 495, defining an outer perimeter of valve 450, and preferably has plurality of convolutes 458, plurality of rib members 459, and circumferential baffle 494. Plurality of rib members 459 each preferably extend radially at least a portion of the distance between peripheries of the base of valve extension 452 and valve ring 495, preferably symmetrically positioned spaced-apart from each other. Preferably, plurality of rib members 459 preferably extend between the base of valve extension 452 and circumferential baffle 494.

Figure 11:
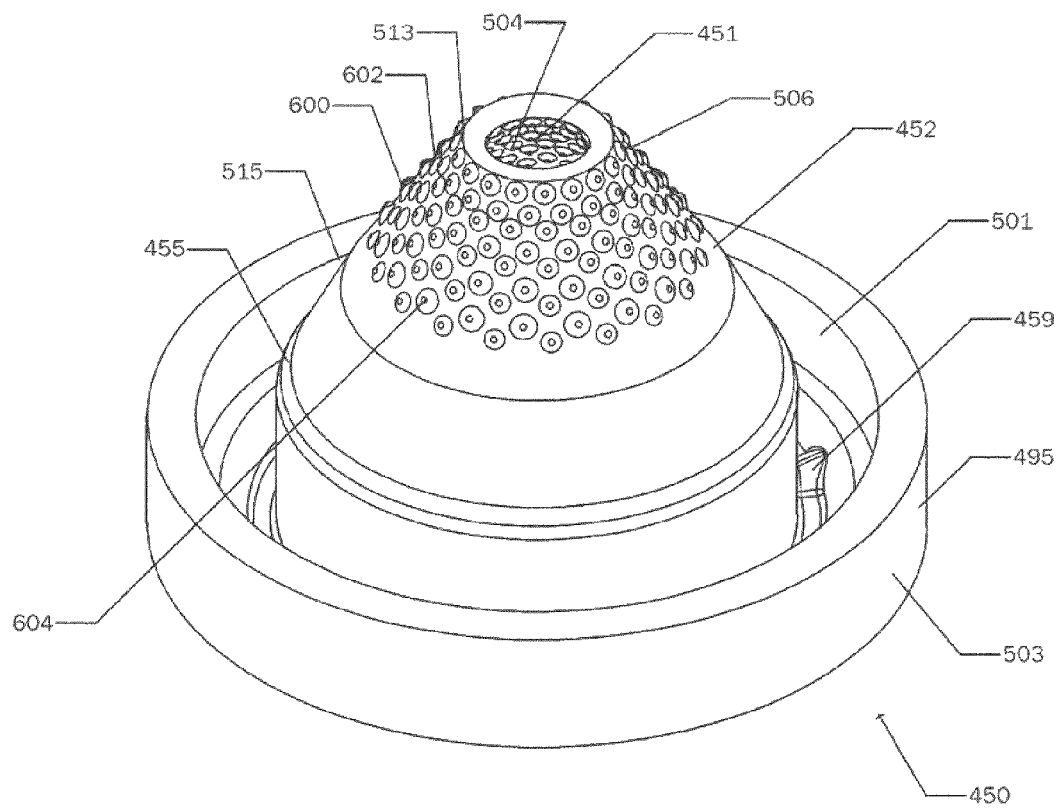
FIG. 11 is a perspective view of a valve according to an embodiment of the present disclosure.
Figure 12:
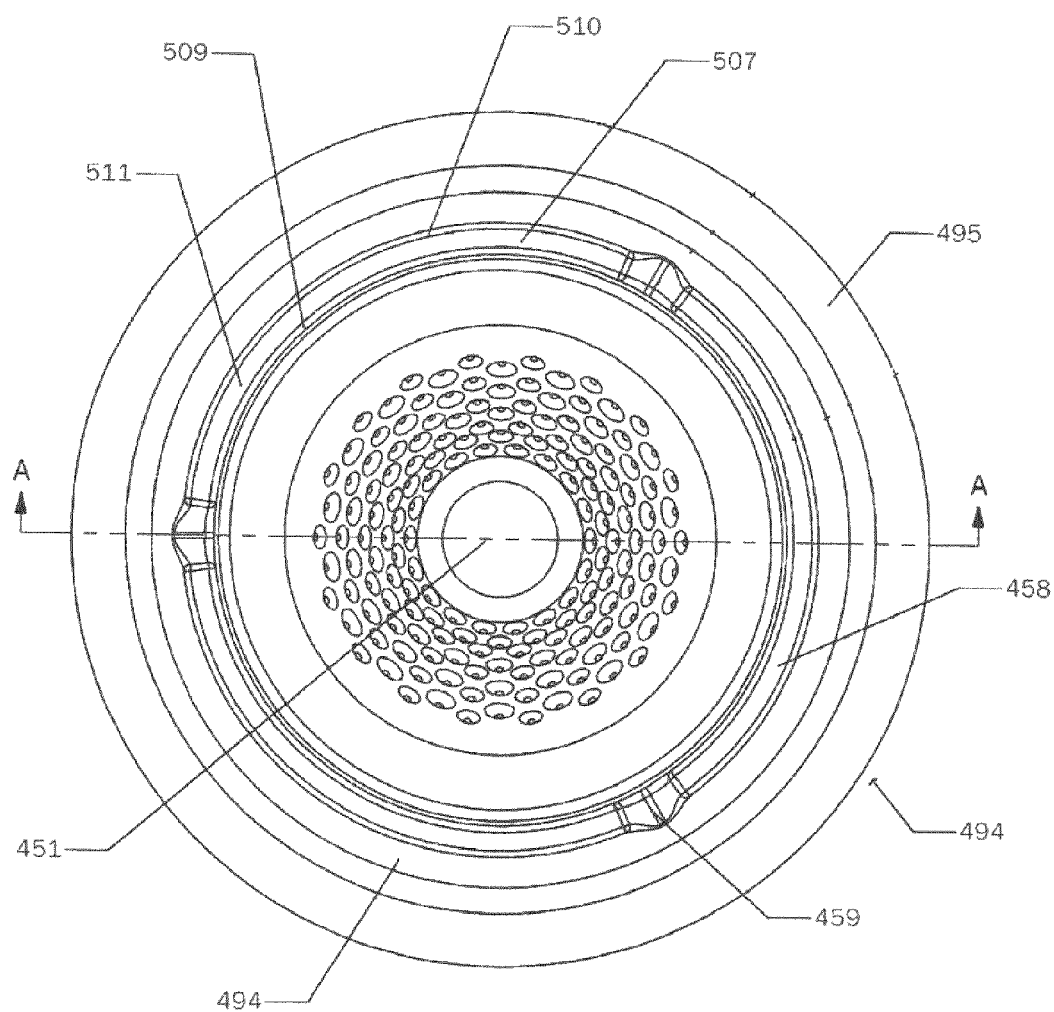
FIG. 12 is a proximal view of the valve of FIG. 11.
Figure 13:
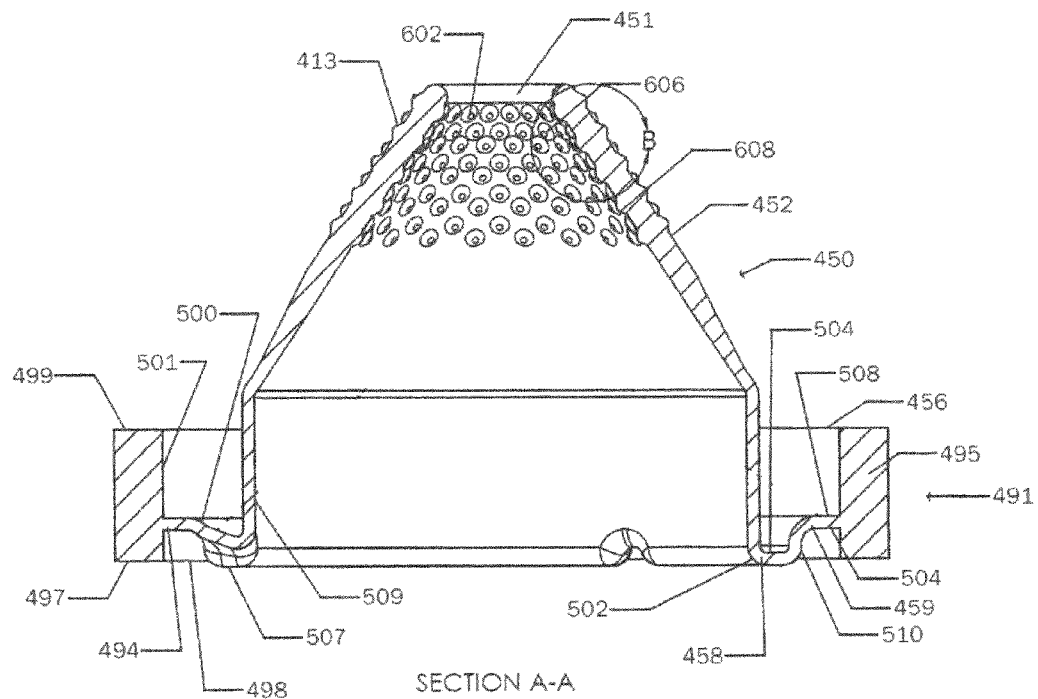
FIG. 13 is a cross-sectional view, taken along line A-A of the valve of FIG. 11, according to an embodiment of the present disclosure.
Figure 14:
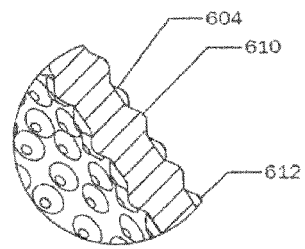
FIG. 14 is a magnified, cut-away surface view of the valve of FIG. 13, according to an embodiment of the present disclosure.

Thus, the proximal valve section 191 or 491 includes valve ring 195 or 495, respectively, positioned in the valve ring recess 179 (FIG. 2) or 479 of the valve housing 132. Referring now to FIG. 11, valve ring 495 has proximal surface 497, distal surface 499, inner perimeter surface 501, and an outer perimeter surface 503 defining an outer perimeter of valve body 455. Proximal valve section 491 preferably has circumferential baffle 494 extending radially inwardly from inner perimeter surface 501 of valve ring 495 to outer sidewall 510 of plurality of convolutes 458. Proximal valve section 491 can include plurality of convolutes 458, each having outer sidewall 510 extending from circumferential baffle 494, first sidewall 507 extending axially and radially inwardly from outer sidewall 510, and a second sidewall 509 extending axially from first sidewall 507, substantially parallel to or slightly angled from inner perimeter surface 501 of valve ring 495, and forming an inner radial periphery of proximal valve section 491.

Proximal surface 498 and distal surface 500 of periphery valve section 456 are each further defined by two sub-elements surfaces, wherein first sub-element surface 502 of proximal surface 498 is defined in a first plane and proximate the inner perimeter of periphery valve section 456, and second sub-element surface 504 of proximal surface 498 is defined in a second plane and proximate the outer perimeter of periphery valve section 456. A similar, but opposing relationship exists between two sub-element surfaces of distal surface 500, wherein first sub-element surface 506 of distal surface 500 is defined in a first plane and proximate the inner perimeter of periphery valve section 456, and second sub-element surface 508 of distal surface 500 is defined in a second plane and proximate the outer perimeter of periphery valve section 456. Accordingly, neither proximal surface 498 nor distal surface 500 of periphery valve section 456 is flat.

Periphery valve section 456 may include circumferential baffle element 494, wherein second sub-element surface 504 of proximal surface 498 and second sub-element surface 508 of distal surface 500 are components thereof. That is, circumferential baffle element 494 is preferably related to proximal valve section 491 of valve 450, wherein circumferential baffle element 494 is defined in the second plane proximate the outer perimeter of periphery valve section 456. Proximal valve section 491 of valve 450 can also include plurality of convolutes 458, each having outer sidewall 510 extending axially from the second plane and circumferential baffle element 494 to the first plane and first sidewall 507. Outer sidewall 510, first sidewall 507, and the second sidewall 509 of each of the plurality of convolutes 458 form a respective convolute recess 511. The proximal valve section 491 can also include a plurality of rib members 459, each radially extending from circumferential baffle element 494 to inner perimeter surface 501 of the valve ring 495 and symmetrically positioned spaced-apart from each other.

The distal valve section 493 can extend axially from proximal valve section 491 and can include valve extension 452 extending axially from the plurality of convolutes 458. The valve extension 452 can have a proximal end portion 512 substantially connected to a distal portion of each of the plurality of convolutes 458, a distal end portion 513, and a medial portion 515 connected to and extending therebetween. According to an embodiment of the valve extension 452, medial portion 515 can have a substantially frusto-conical or other similar conical-form shape, as illustrated. The distal valve section 493 includes valve opening 451 positioned in distal end portion 513 of valve extension 452, which can have, for example, an annular shape. The valve opening 451 is adapted to individually and separately receive therethrough any one of the plurality of different elongate tools (not shown) each having a different diameter so that when any one of the plurality of elongate tools is positioned through valve opening 451, a septum-type seal is maintained between peripheries of distal end portion 513 of valve extension 452 surrounding valve opening 451 and outer peripheries of any one of the plurality of elongate tools when extending therethrough. As noted previously, the plurality of tools each have an elongate body for extending through valve housing 132, valve opening 451 of valve 450, and the cannula 40.

The plurality of convolutes 458 are each positioned between and connected to any two adjacent rib members 459. According to an embodiment of the convolutes 458, each convolute 458 can be in a selected biased position before and after each of the plurality of different elongate tools, individually and separately, extends through the valve opening 451. According to an embodiment of the present invention, the combination of the convolutes 458, circumferential baffle 494 and valve extension 452 allow for axial movement of the tools without a corresponding movement within valve opening 451 with respect to outer peripheries of the tools.

The valve body 455, in general, and the portion of valve extension 452 surrounding opening 451, in particular, can be formed of a flexible material to provide the elastic range necessary to accommodate the plurality of elongate tools. According to an embodiment of valve body 155, the flexible material advantageously can include a silicon material coated with paralene, available through various manufacturers, including Dow Corning Corp., to enhance the strength of the valve 450 and to enhance sliding and sealing of the plurality of tools.

A method of forming a trocar system 420, as constructed, for example, the valve 450 advantageously has a stretching or elastic range to readily accommodate, e.g., auto-reduction, tools or other instruments having a diameter of about 5 millimeters to about 15 millimeters as understood by those skilled in the art while still maintaining pneumoperitoneum. The valve opening 451 of the valve body 455 has a diameter less than the diameter of each of the tools that extend through valve 450 so that a secured seal is provided around outer peripheries of each of the tools. The second valve 160 advantageously has this range as well, but individually can even have a greater range, e.g., 1 millimeter to 13 or 14 millimeters. Accordingly, with valve 450 and second valve 160, in combination, the trocar system 420 advantageously can receive different diameter instruments without the necessity of switching cannulas or valve systems.

Embodiments of the present invention also include a method of using a trocar system 420, as with prior art trocar system 120, including the steps of providing a cap assembly 130, which includes valve 450, or 150, as described above, and inserting a tool through the valve 450, or 150, and cap assembly 130. During the insertion through improved valve 450, circumferential baffle 494, convolutes 458 and valve extension 452 flex so that valve body 455 extends distally by contact pressure from the tool and so that a distal end of the tool is guided through valve opening 451. The circumferential baffle 494 and symmetric rib structure reinforces the movement of convolutes 458 and the recovery of convolutes 458 once the tool is extended through valve opening 451. Because valve 450 is constructed in a thin and relatively conical shaped profile, valve 450 functions like a thin elastic membrane that flexes inwardly and outwardly along a fairly wide range of tool positions, without requiring valve opening 451 to "slide" along the outer peripheries of the respective tool once positioned through valve opening 451, and does not float or rotate in the valve housing 132. This method also includes extending the tool through a cannula body 42 matingly connected to the cap assembly 130 at a proximal portion 48 thereof. The method further includes the steps of detaching the cap assembly 130 from the cannula body 42 and removing tissue or other specimen as understood by those skilled in the art from the cannula body 42. Because various types and diameters of tools can be used by medical personnel, embodiments of a valve advantageously allow one type of valve, cannula, or trocar system to be readily used for all of these various sizes and types of tools.

As noted, valve body 455, in general, and the portion of valve extension 452 surrounding opening 451, in particular, can be formed of a flexible material to provide the elastic range necessary to accommodate the plurality of elongate tools. According to an embodiment of valve body 455, the flexible material advantageously can include a silicon material coated with paralene, available through various manufacturers including Dow Corning Corp., to enhance the strength of valve 450 and to enhance sliding and sealing of the plurality of tools. Because ease of insertion and removal of the instruments is an important aspect during use of cannula 40, and because even small measures of improvement can translate into realized enhancement of performance, coatings and other measures directed toward improving lubricity can be advantageously supplemented, wherein a reduction in electrostatic adhesion between valve 450 and the plurality of tools can serve to further enhance the ease of insertion and removal.

Figure 10:
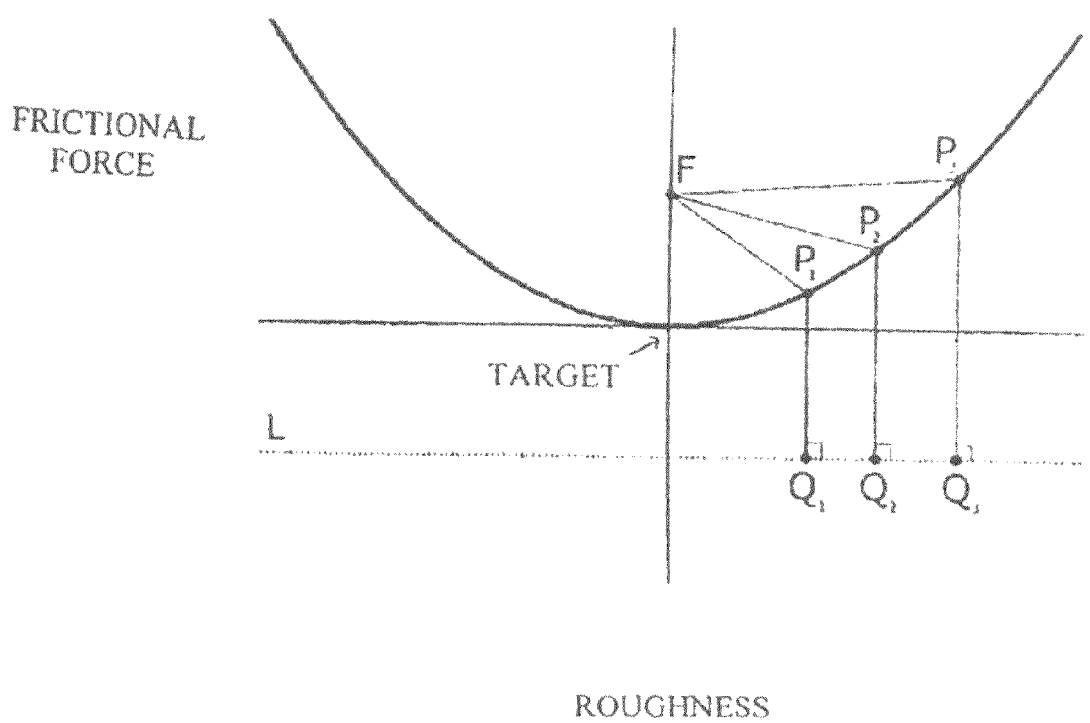
FIG. 10 is a graphical representation of the parabolic relationship between frictional force and roughness.

The relationship between frictional force and roughness is parabolic, as depicted in FIG. 10, wherein frictional forces are increased between both very smooth, as well as very rough surfaces, and wherein at the vertex of the parabola, a target roughness quality is represented that results in little or no frictional force. The smoothness of valve extension 452, therefore, can be specifically adjusted relative to previously described valve extension 152', such as seen in FIGS. 7-9, wherein plurality of friction-reduction features 300 were defined, but, as will be further discussed, are presently improved. That is, prior valve body 155', in general, and the portion of the valve extension 152' proximate opening 151' included plurality of friction-reduction features 300 to advantageously minimize electrostatic forces between instruments and the valve 150'. The plurality of friction-reduction features 300 was configured to increase roughness of valve extension 152' in such a manner that movement toward the vertex along the demonstrated parabolic curve relating frictional force and roughness can be realized, wherein plurality of friction-reduction features 300 was comprised of plurality of protrusions 302, defined on outer surface 304 and inner surface 306 of valve extension 152', generally over an area defined proximate and between medial portion 215' and distal end portion 213' of valve 150'. The friction-reduction features 300 were defined proximate the apical end of the valve 150' in anticipation of contact with the plurality of elongate tools extended therethrough, and were further defined on both opposing surfaces 304-306 in order that advantageous minimization of electrostatic forces may be realized also during contact between the valve body 155' and the second valve 160. The plurality of protrusions 302 were tear-drop shaped, to functionally improve the prior manufacturing process, as well as serving to reduce the resistive forces between the contact surfaces of an inserted instrument and the valve 150' without compromise to the septum seal or to the inherent flexibility and adaptability of the valve 150'.

Referring now to FIGS. 11-14, improved conical valve 450 preferably has plurality of closely and symmetrically spaced friction-reduction features 600, wherein increased concentration and relative proximity of friction-reduction features 600 was empirically determined to enhance minimization of electrostatic forces between instruments and valve 450. Friction-reduction features 600 are preferably protrusions formed on inner and outer surfaces, 504 and 506, respectively, of conical valve 450, proximate distal end 413 and valve opening 451. Preferably, first circumferential row 602 of protrusions 604 is defined proximate valve opening 451 in a closely-spaced, essentially abutting conformation, whereafter second circumferential row 606 of protrusions 604 is defined in a position of greater distance from valve opening 451 relative to first circumferential row 602, wherein the same total number of protrusions 604 is preferably defined in second row 606 as first row 602, but given the increased diameter of conical valve 450 at the location of second row 606 relative to that of first row 602, protrusions 604 of second circumferential row 606 are less closely-spaced than those of first circumferential row 602. Thereafter, further plurality of rows 608 are defined in similar fashion. The positioning of the protrusions 604 of each adjacent circumferential row 608 may also be juxtaposed, such that a radial twist pattern may be defined by the protrusions 604 about conical valve 450 proximate distal end 413 and valve opening 451.

Protrusions 604, as noted, may be formed in essentially any shape capable of maintaining the preferred functionality of creating additional space between valve 450 and an instrument inserted therein, and thereby reducing surface area for frictional contact therebetween. Moreover, protrusions 604 may be formed according to a multi-shot liquid silicone rubber process, wherein liquid silicone rubber may be utilized for formation of valve body 455 and traditional thermoplastic elements may be utilized for formation of protrusions 604, thus combining materials of differing coefficients of friction in a single molded part. In such manner, protrusions 604 may perform with action similar to that of ball bearing elements.

A further improvement proximate distal end 413 of valve 450 relates to the definition of the plurality of friction-reduction features 600 definition on both inner surface 504 and outer surface 506 of the distal end 413 of valve 450, wherein each of the plurality of protrusions 604 is preferably shaped as a round-tipped cone 610, wherein the position and shape of friction-reduction features effectively and measurably enhances friction reduction. That is, kinetic friction between valve 450 and related instruments is advantageously minimized as valve opening 451 is deformed temporarily by contact pressure from the tool, wherein contact area between valve 450 and the instruments is reduced.

Moreover, elongation or other reactive force redirection by circumferential baffle 494 serves to minimize deformation of the valve opening as well. The friction-reduction features 600, especially with circumferential baffle 494, ribs 459, and convolutes 459, can reduce the resistive forces between the contact surfaces of an inserted instrument and valve 450 without compromise to the septum seal or to the inherent flexibility and adaptability of valve 450 of the present invention, wherein a broad endoscopic instrument diameter range, from about 5 mm to 15 mm diameter, can be successfully accepted. The friction-reduction features 600 are preferably defined proximate the apical end of valve 450, in anticipation of contact with the plurality of elongate tools extended therethrough, and are further preferably defined on both opposing surfaces 504 and 506 in order that advantageous minimization of electrostatic forces may be realized also during contact between valve 450 and second valve 160.

Each protrusion 604 is thus preferably shaped with a generally circular base and extending outward from inner and outer surfaces 504 and 506, respectively, of valve 450, to form cone 610, preferably with a rounded tip 612. This preferred shape also serves to facilitate the manufacturing process, wherein successful formation and ejection of valve 450 from a mold is achieved more readily. Thus, while it is recognized that other shapes could be utilized, the preferred round-tipped cone shape is preferred. Further, while the arrangement of plurality of protrusions 604 is depicted and described according to the preferred configuration, wherein a particular enhanced roughness quality is achieved, with measurable improvements over previous configurations, relative to frictional force, other arrangements could be utilized, including more rows, aligned rows, non-rows and/or an arrangement of protrusions with even closer relative proximity, even approaching or achieving an essentially solid configuration, such as an annular rib; however, resulting modification to the roughness and/or related electrostatic nature of the surface could influence the achieved performance enhancement relative to the preferred configuration.

Having thus described exemplary embodiments of the present invention, it should be noted by those skilled in the art that the within disclosures are exemplary only, and that various other alternatives, adaptations, and modifications may be made within the scope of the present disclosure. Accordingly, the present disclosure is not limited to the specific embodiments illustrated herein, but is limited only by the following claims.

We claim:

1. A valve, comprising:
   a valve body having a proximal end and a distal end;
   a valve ring connected to said proximal end of said valve body;
   a plurality of convolutes defined proximate to and extending around said valve body;
   a plurality of ribs defined proximate and sequentially spaced relative said plurality of convolutes, and extending between said valve body and said valve ring; and
   a plurality of friction-reduction features defined proximate said distal end of said valve body, wherein said friction-reduction features are formed at one of an inner surface and an outer surface of said valve body.

2. A valve, comprising:
   a valve body having a proximal end and a distal end;
   a periphery valve section connected to and extending outwardly from a periphery of said proximal end of said valve body;
   at least one convolute defined within said periphery valve section;
   a plurality of rib members radially extending at least a portion of the distance between said periphery of said valve body and an outer perimeter of said periphery valve section; and
   a valve ring;
   wherein said valve body further comprises a valve extension extending axially away from said plurality of convolutes;
   wherein said valve extension further comprises a distal end portion, a proximal end portion substantially connected to a distal portion of said plurality of convolutes, and a substantially conically shaped medial portion connected to and extending between said distal end portion and said proximal end portion of said valve extension;
   an annular-shaped valve opening in said distal end portion of said valve extension; and
   a plurality of friction-reduction features proximate said distal end portion of said valve extension and said valve opening;
   wherein said plurality of friction-reduction features is a plurality of closely and symmetrically spaced friction-reduction features, wherein said friction-reduction features are formed at one of an inner surface and an outer surface of said valve extension.

3. The valve of claim 2, wherein said valve ring further comprises a proximal surface, a distal surface, and an outer perimeter surface,
   wherein said valve ring defines an outer perimeter of said periphery valve section and of said proximal end of said valve body,
   wherein periphery valve section further comprises a proximal surface and a distal surface, and
   wherein said proximal surface and said distal surface of said periphery valve section each further comprise two sub-element surfaces.

4. The valve of claim 3, wherein a first sub-element surface of said proximal surface of said periphery valve section is defined in a first plane and is proximate an inner perimeter of said periphery valve section, and said second sub-element surface of said proximal surface is defined in a second plane and is proximate said outer perimeter of said periphery valve section.

5. The valve of claim 3, wherein a first sub-element of said distal surface of said periphery valve section is defined in a first plane and is proximate an inner perimeter of said periphery valve section, and said second sub-element surface of said distal surface is defined in a second plane and is proximate said outer perimeter of said periphery valve section.

6. The valve of claim 3, wherein neither said proximal surface of said periphery valve section nor said distal surface of said periphery valve section is flat.

7. The valve of claim 4, wherein at least a portion of plurality of convolutes is defined in a first plane and a second plane proximate said periphery valve section.

8. The valve of claim 2, wherein said at least one convolute is a plurality of convolutes, wherein each said convolute of said plurality of convolutes further comprises a first sidewall extending radially inwardly from a portion of said valve ring and a second sidewall extending axially from said first sidewall and substantially parallel to an inner perimeter surface of said valve ring, wherein said plurality of convolutes form an inner radial periphery of a proximal valve section of said cannula valve, and wherein each said convolute of said plurality of convolutes is positioned between any two adjacent of said plurality of rib members.

9. The valve of claim 2, further comprising at least one convolute recess formed by an inner perimeter surface of said periphery valve section and a first sidewall and a second sidewall of said at least one convolute.

10. The valve of claim 2, wherein said plurality of rib members is symmetrically spaced-apart from each other.

11. The valve of claim 2, wherein said plurality of rib members extends radially from an inner radial periphery of said proximal end of said valve body to an outer perimeter of said plurality of convolutes, respectively.

12. The valve of claim 2, wherein each said friction-reduction features is a round-tipped cone.

13. The valve of claim 2, wherein a first circumferential row of said plurality of friction-reduction features is defined proximate said valve opening, wherein a second circumferential row of said plurality of friction-reduction features is defined in a position of greater distance relative to said valve opening relative than said first circumferential row, and wherein a total number of said plurality of friction-reduction features in said first circumferential row is equal to a total number of said plurality of friction-reduction features in said second circumferential row, and said plurality of friction-reduction features in said first circumferential row are more closely spaced together than said plurality of friction-reduction features of said second circumferential row.

14. The valve of claim 2, wherein said plurality of friction-reduction features is formed from a first material having a first coefficient of friction, said valve body being formed from a second material having a second coefficient of friction, wherein said first coefficient of friction does not equal said second coefficient of friction.

15. The valve of claim 2, wherein said valve body is formed from a first material and said plurality of friction-reduction features is formed from a second material, and wherein said valve body and said friction-reduction features are formed as a single molded part comprised of differing coefficients of friction, wherein said first material is an elastomeric material.

16. The valve of claim 2, wherein each of said plurality of friction-reduction features further comprises a generally circular base and extends outwardly from said inner surface and said outer surface of said valve body to a friction-reduction features tip, said tip having a diameter that is smaller than a diameter of said generally circular base.

17. The valve of claim 2, further comprising a plurality of circumferential rows of said plurality of friction-reduction features, wherein each said circumferential row is juxtaposed relative to an adjacent circumferential row, and wherein a radial twist pattern is defined by said plurality of friction-reduction features about said valve body proximate said distal end portion and said valve opening.

18. A valve, comprising:
a valve body having a proximal end and a distal end;
a valve opening formed at said distal end of said valve body;
a valve ring connected to said proximal end of said valve body;
a plurality of convolutes intermediately positioned between said valve body and said valve ring; and
a plurality of ribs extending outwardly from said valve body and spanning across said plurality of convolutes respectively;
wherein, when said valve body is stretched, said plurality of convolutes cooperate with said plurality of ribs and thereby return said valve opening at a substantially original shape; and
a plurality of friction-reduction features formed at one of an inner surface and an outer surface of said valve extension.

19. The valve of claim 18, wherein said plurality of friction-reduction features is formed from a first material having a first compression set, said valve body being formed from a second material having a second compression set, wherein said first compression set does not equal said second compression set.

* * * * *